(12) United States Patent
Dang et al.

(10) Patent No.: US 12,133,916 B2
(45) Date of Patent: Nov. 5, 2024

(54) PROCESS FOR PRODUCING AN ANDROGRAPHOLIDE CARRIER SYSTEM

(71) Applicant: Nam Hai Lai, Ho Chi Minh (VN)

(72) Inventors: Hong Ngoc Thi Dang, Ho Chi Minh (VN); Nam Hai Lai, Ho Chi Minh (VN)

(73) Assignee: Nam Hai Lai, Ho Chi Minh (VN)

( * ) Notice: Subject to any disclaimer, the term of this patent is extended or adjusted under 35 U.S.C. 154(b) by 419 days.

(21) Appl. No.: 17/693,271

(22) Filed: Mar. 11, 2022

(65) Prior Publication Data

US 2023/0105782 A1    Apr. 6, 2023

(30) Foreign Application Priority Data

Oct. 5, 2021  (VN) .............................. 1-2021-06212

(51) Int. Cl.
| | | |
|---|---|---|
| *A61K 9/107* | (2006.01) | |
| *A61K 47/10* | (2017.01) | |
| *A61K 47/14* | (2017.01) | |
| *A61K 47/26* | (2006.01) | |
| *A61K 47/32* | (2006.01) | |
| *A61K 47/38* | (2006.01) | |

(52) U.S. Cl.
CPC ............ *A61K 9/1075* (2013.01); *A61K 47/10* (2013.01); *A61K 47/14* (2013.01); *A61K 47/26* (2013.01); *A61K 47/32* (2013.01); *A61K 47/38* (2013.01)

(58) Field of Classification Search
CPC ...... A61K 9/1075; A61K 47/10; A61K 47/14; A61K 47/26; A61K 47/32; A61K 47/38; A61K 9/5146; A61K 9/5161; A61K 9/5138
See application file for complete search history.

(56) References Cited

PUBLICATIONS

Antibacterial Activity of Ethanol Extract of Andrographis paniculate, Indian Journal of Pharmaceutical Sciences, 2009 (Year: 2009).*

* cited by examiner

*Primary Examiner* — Robert A Wax
*Assistant Examiner* — John Seungjai Kwon
(74) *Attorney, Agent, or Firm* — Fulwider Patton LLP

(57) ABSTRACT

The present invention relates to a method for producing an andrographolide carrier system, comprising: (i) preparing a dispersed phase by dissolving andrographolide in ethanol solvent; (ii) preparing an inner encapsulating carrier layer; (iii) forming a protective encapsulating layer of the active agent; (iv) forming bonds to attach mucoadhesion enhancers onto the surface structure of the encapsulating layer, and then bringing the mixture to room temperature, slowly adding hydroxypropyl methylcellulose HPMC; (v) heating until the temperature reaches 50° C., adding Polysorbate 80 and PEG-40 hydrogenated castor oil to the mixture, with further stirring under vacuum; and (vi) filtering the product by injection through a nanofilter system.

1 Claim, 1 Drawing Sheet

PROCESS FOR PRODUCING AN ANDROGRAPHOLIDE CARRIER SYSTEM

CROSS-REFERENCES TO RELATED APPLICATIONS

This application claims priority from Vietnam Patent Application No. 1-2021-06212, filed Oct. 5, 2021, the content of which is incorporated by reference herein in its entirety.

FIELD OF INVENTION

The present invention relates to a process for producing an andrographolide carrier system.

BACKGROUND OF INVENTION

Andrographolide (AG) is a compound extracted from the annual herbaceous plant *Andrographis*, with the scientific name of *Andrographis paniculata* (*A. paniculata*). From this plant is produced an herb that has been traditionally used in Chinese medicine as well as in some Asian countries to treat a number of health related problems such as cancer, rheumatoid arthritis, diarrhea, respiratory infection, laryngitis, etc., especially in treatment of acute respiratory infection.

Andrographolide belongs to the group of diterpenoid lactone compounds with the functional group α-alkylidene c-butyrolactone, with 3 hydroxyl residues at positions C-3, C-14 and C-19, with the chemical structure as shown below:

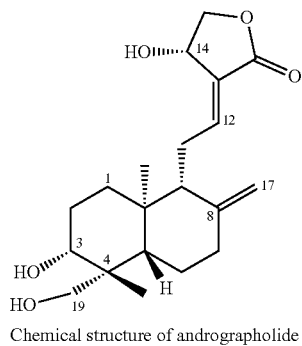 [SMILES: C=C1CC[C@@H]2[C@](C)(CO)[C@H](O)CC[C@@]2(C)[C@@H]1C/C=C1/C(=O)OC[C@H]1O]

Chemical structure of andrographolide

Andrographolide in a suitable dose has proved that it is capable of anti-inflammation, which has a potential application in the treatment of many diseases such as peptic ulcer disease, respiratory inflammation, etc. Andrographolide also has a potential antiviral effect in the treatment of COVID-19, and can reduce the level of inflammation in the patient, improve respiratory symptoms, suppress the virus and improve the body's immunity, etc., with great safety. However, andrographolide is a water-insoluble compound that is susceptible to denaturation under the impacts of heat and light, and the chemotherapeutic applications of AG are extremely limited because of its poor bioavailability, short plasma half-life, and inappropriate tissue localization.

Therefore, it is necessary to reduce the denaturation of the compound when used, especially orally, improve its absorbability, and increase its bioavailability. The application of carrier granulation technology is a new technology application to produce a drug delivery system and increase the bioavailability of a compound. This process creates a new system with a structure comprising very small (nano) spherical micelles. Its core contains active nutrients and is outer encapsulated, and thus is capable of containing, protecting, transporting, and releasing active agents. The outer layer structure that allows adhesion to the mucosal walls precisely delivers the compound to desired sites within the body. Andrographolide packed in a drug delivery system helps to selectively, effectively, and economically deliver the compound to the targets. In Vietnam, the technology for producing a carrier system is still new in biomedicine, and does not yet have many applications, but has attracted a lot of research interests. Currently, the most popular studies are about the application of nano curcumin and the drug delivery systems to targeted cells, and there has not been any study on the production of nano andrographolide. The use of a carrier system to carry drug and release drug is a new direction to treat diseases and apply in other products.

In the study by Partha Roy et al. in 2010, AG nanoparticles (AGnp) were loaded in 50:50 poly(DL-lactide-co-glycolic acid). Photon correlation spectroscopy showed that the average particle size was 173 nm and the zeta potential was −34.8 mV. In this study the particle size was larger than 100 nm, with a complex procedure employed only experimentally.

In the study by Partha Roy et al. in 2013, PLGA nanoparticles were loaded with AG, with the resulting particle size of 181±12.6 nm with the study aiming at producing microemulsions. However, the particle size was still larger than 100 nm, with complex procedures employed only experimentally.

A study by Yandi Syukri et al. in 2018 was on a Nano Self-Emulsifying Drug Delivery System (SNEDDS) of andrographolide using Capryol-90, Tween 20, and polyethylene glycol (PEG) 400 to produce particles of less than 100 nm. However, the problem with the storage capacity of the particles when administered orally has not been resolved. The particle structure needed to be adjusted to be effective as an oral drug.

Known processes for producing nano andrographolide produce large, non-uniform micelles, especially nano andrographolide formulated with a size larger than 150 nm, so the water-solubility efficiency and use efficiency are not high. For particles of less than 100 nm, the problem is that the capacities for storage and no clearance during use are inefficient.

Therefore, there is a demand for a process for producing a microemulsion system comprising uniform micelles of less than 100 nm with better water-solubility while retaining the structure, and the activity of andrographolide during production, more specifically, improvement of the storage capacity in the digestive tract, reduces drug clearance when administered orally, thereby improving the andrographolide-use efficiency.

SUMMARY OF INVENTION

It is an object of the present invention is to provide a process for producing an andrographolide carrier system in order to overcome the disadvantages of known processes for producing uniform water-soluble particles of less than 100 nm, wherein the activity and structure remains unchanged. And at the same time, it is beneficial to provide capacities for adhesion and storage of the compound in the digestive tract to allow for an increase in use efficiency of andrographolide active agents, asorbability, and bioavailability, and slow down the clearance, especially improving asorbability via oral administration.

To achieve the above object, the present invention provides a process for producing an andrographolide carrier system (also referred to as Anmoniliv) that comprises the following steps:

(i) Step 1: preparing a dispersed phase by dissolving andrographolide in ethanol solvent in a mass ratio of andrographolide to ethanol of (6-10):(8-12), preferably of (7-9):(9-11), most preferably of 8:10, by a stirrer at 300-500 rpm while heating to 40-60° C. for 4-8 hours.

(ii) Step 2: preparing an inner encapsulating carrier layer to protect active agent by heating liquid PEG (polyethylene glycol) to 60-80° C., with constant stirring for 15-30 minutes.

(iii) Step 3: forming a protective encapsulating layer of the active agent by adding the carrier to the dispersed phase in a mass ratio of (35-45):(55-65), preferably of (38-42):(58-62), most preferably of 40:60, with further heating of the carrier-dispersed phase mixture to 40-60° C., while stirring at 400-800 rpm for 30-60 minutes.

(iv) Step 4: forming bonds to attach mucoadhesion enhancers onto the surface structure of the encapsulating layer by adding poly(acrylic acid) to the mixture in a ratio of (1-20):(85-95), most preferably of 10:90, with stirring at 400-800 rpm for about 30 minutes to attach the poly(acrylic acid) to the surface of the encapsulating layer. Then the mixture is brought to room temperature, hydroxypropyl methylcellulose (HPMC) is slowly added to the mixture in a ratio of (1-10):(85-95), to increase the expansion coefficient and adhesion force, and improve the release of adhesive poly(acrylic acid), to form cross-linkage with hydroxypropyl methylcellulose (HPMC), while vigorously stirring the mixture until homogeneous.

(v) Step 5: heating the mixture for 2 hours until the temperature reaches 50° C., adding Polysorbate 80 (TWEEN 80) and PEG-40 hydrogenated castor oil in a ratio of (25-35):(65-75), most preferably of 30:70, to the carrier-dispersed phase mixture obtained in step (iv) in a mass ratio of 40:60, with further stirring at 500-700 rpm under vacuum, wherein the reaction temperature is kept at 50-80° C. for 1-2 hours, controlling the quality of the resulting product by water dissolution and transparency measurement, where if it does not meet quality standards then continue heating and measuring transparency every 30 minutes until transparency is observed to quench the reaction; homogenizing the mixture by injection through a 30 Mpa (300 bar) high-pressure homogenizer.

(vi) Step 6: filtering the product by injection through a nanofilter system before filling and packing; controlling the quality of the resulting product by water dissolution and transparency measurement.

The carrier system of the process according to the invention is further experimented with active agents other than andrographolide, which allows to deliver active agents and targeted- and control-release similar small molecules.

DETAILED DESCRIPTION OF INVENTION

Figure 1:
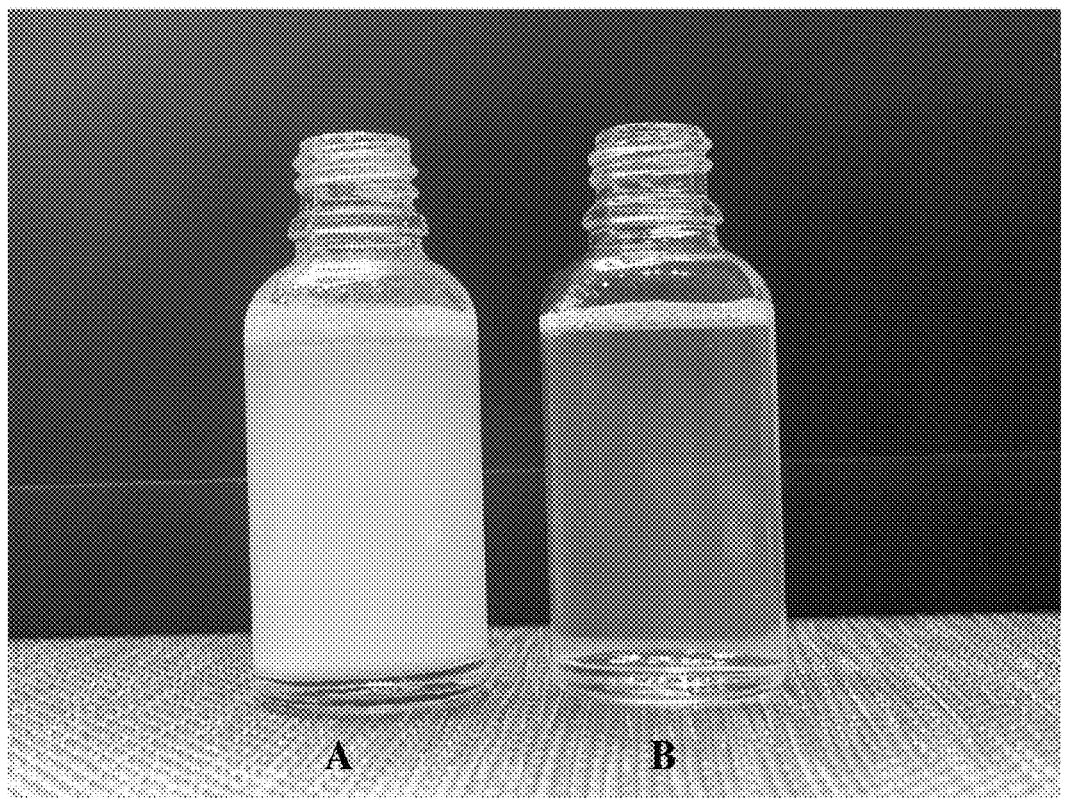
FIG. 1 shows an image comparing the water-dispersability between a known andrographolide and nano andrographolide obtained by a process for producing an andrographolide carrier system of the present invention.

A process for producing an andrographolide carrier system of the present invention is performed as follows:

(i) Step 1: preparing the dispersed phase by dissolving andrographolide in ethanol solvent in a mass ratio of andrographolide to ethanol of (6-10):(8-12), preferably of (7-9):(9-11), most preferably in a mass ratio of 8:10, by a stirrer at 300-500 rpm while heating to 40-60° C. for 4-8 hours.

Ethanol is used as a solvent capable of dissolving andrographolide well, which helps better prepare the dispersed phase and better facilitate the combination of the dispersed phase with the PEG carrier. The use of hydroxyl-(OH—)based ethanol solvent forms bond with water, thus having a stablizing effect on the structure of the oil-in-water emulsion system. By experiments, the inventors have determined that, in an andrographolide:ethanol ratio of (6-10):(8-12) by mass, preferably of (7-9):(9-11) by mass, however, most preferably in an andrographolide:ethanol ratio of 8:10 by mass, andrographolide achieves the highest solubility and excess ethanol solvent resulting in waste is avoided. The use of stirring and heating to produce andrographolide with better dispersibility, when the inventors test under various stirring and temperature conditions, shows that at 300-500 rpm with heating at 40-60° C., the andrographolide dispersed phase is better and better combines with the PEG carrier.

(ii) Step 2: preparing an inner encapsulating carrier layer to protect active agent by heating liquid PEG (polyethylene glycol) to 60-80° C., with constant stirring for 15-30 minutes.

When used, andrographolide is often degraded in the digestive tract, a portion of which absorbed into the blood, while the rest mostly subjected to clearance. Thus, there is a need for a process for producing micelles containing small biofilm andrographolide active agents with stable structure, non-aggregation, and high solubility. Because the andrographolide carrier system of the present invention is employed in pharmaceuticals, the agents selected for use must have great safety, no toxicity, and little side effects.

Surfactants are used to create stability and homogeneity for the system, and prevent agglomeration and adhesion of compounds in the system. Herein polymer carriers used with relatively high drug loads may confer many pharmacokinetic benefits, such as stabilized drugs, which may be administered for treatment over long term by slow drug release in accordance with polymer decomposition, biological distribution of the drugs, targeting ability, penetration through cell membranes, etc., that can be controlled by physicochemical properties of the polymers. Poly(ethylene glycol) (PEG) is a polymer used to prepare drug delivery systems. PEG can significantly change the surface properties of conjugated materials. In the present invention, andrographolide is hydrophobic, there are two strategies for encapsulation and film formation for the PEG encapsulating layer on the surface: (1) PEG physically adheres to the compound by physical adsorption, including electrostatic or hydrophobic interactions; (2) PEG can conjugate with hydrophobic molecules in the andrographolide molecular structure to form macromolecules that can self-assemble themselves or with other compounds for PEGylation in the solution. As a result of the binding effect of said two mechanisms, PEG used herein will allow the production of a stable carrier system for andrographolide as well as some water-insoluble active agents with similar properties.

(iii) Step 3: forming a protective encapsulating layer of active agent by adding the carrier to the dispersed phase in a mass ratio of (35-45):(55-65), preferably of (38-42):(58-62), most preferably of 40:60, with further heating of the carrier-dispersed phase mixture to 40-60° C., while stirring at 400-800 rpm for 30-60 minutes.

(iv) Step 4: forming bonds to attach mucoadhesion enhancers onto the surface structure of the encapsulating layer by adding poly(acrylic acid) to the mixture in a mass ratio of (1-20):(85-95), most preferably of 10:90, with stirring at 400-800 rpm for 30-60 minutes to attach poly (acrylic acid) onto the surface of the encapsulating layer.

Conventional structures enhance absorbability, but capacities for storage and retention in the digestive tract when administered orally are not optimal, as they are subjected to clearance. Polyacrylic acid has an excellent mucoadhesive property because of the presence of a large number of carboxylic acid groups, which can form hydrogen bonds with mucin oligosaccharide side chains, and form physical bonds between polymer chains and mucous layers. It is beneficial to promote adhesion to the mucous membrane. Poly(acrylic acid) is a synthetic cross-linked polymer of acrylic acid. With the acrylic acid group, it is hardly affected by temperature and microorganisms, non-toxic, and non-irritating and safe. A survey study has shown that the higher the compound content, the stronger the adhesion to the mucous membrane of the drug delivery system, and a small amount of hydroxypropyl methylcellulose (HPMC) is mainly used to control drug release.

Then the mixture is brought to room temperature, hydroxypropyl methylcellulose (I-PMC) is slowly added to the mixture in a mass ratio of (1-10):(85-95), to increase the expansion coefficient and adhesion force, and improve the release of adhesive poly(acrylic), to form cross-linkages with hydroxypropyl methylcellulose (HPMC), and it is necessary to vigorously stir the mixture until homogeneous.

A carrier structure with surface bonds with poly(acrylic acid) and hydroxypropyl methylcellulose is formed to increase the adhesion of the mucous membrane and mucoadhesion ability, improve the drug release, and reduce the clearance, thereby increasing the use efficiency.

(v) Step 5: heating the mixture until the temperature reaches 50° C., adding Polysorbate 80 (TWEEN 80) and PEG-40 hydrogenated castor oil in a mass ratio of (25-35): (65-75), most preferably of 30:70, to the carrier-dispersed phase mixture obtained in step (iv) in a mass ratio of 40:60, with further stirring at 500-700 rpm under vacuum, wherein the reaction temperature is kept at 50-80° C. for 1-2 hours, controlling the quality of the resulting product by water dissolution and transparency measurement, where if it does not meet quality standards then continue heating and measuring transparency every 30 minutes until transparancy is observed to quench the reaction. Then, the mixture is homogenized by injection via a 30 Mpa (300 bar) high-pressure homogenizer.

By theoretical and experimental studies, it has been found that to produce nano andrographolide with good water solubility, the emulsion system should be in the form of an oil-in-water emulsion. The emulsifier selection to increase the stability of the microemulsion system is based on the properties thereof (in the form of oil-in-water microemulsion system, in the form of water-in-oil microemulsion system, etc.). Therefore, an emulsifier as Polysorbate 80 and PEG-40 Hydrogenated Castor Oil is selected in a ratio of 30:70, because Polysorbate 80 and PEG-40 hydrogenated castor oil are both hydrophilic, non-toxic, and highly safe agents, however, when used alone, the use efficiency of the formation of nanostructures is not high, the reaction time is long, and it is not suitable in industrial-scale production. A lot of studies have been carried out to determine the ratio of Polysorbate 80 and hydrogenated castor oil PEG-40 to form stable polymer chains.

Since the emulsifier Polysorbate 80 and PEG-40 hydrogenated castor oil are molecules with two distinct portions, an oleophilic portion and a hydrophilic portion, it is capable of forming a bond with andrographolide and carrier mixture. The oleophilic portion of Polysorbate 80 and PEG-40 hydrogenated castor oil forms a bond with andrographolide and the hydrophilic portion forms a bond with the hydrophilic portion of the mixture of the PEG carrier, thus forming andrographolide micelles, and with which structure maintaining good protection of andrographolide activity.

An andrographolide microemulsion carrier system is produced by stirring at 400-600 rpm under vacuum, wherein the reaction temperature is kept at 100° C. for 1-2 hours, then emulsification of the entire mixture for 30 minutes at 400-800 rpm. The combination of Polysorbate 80 and PEG-40 hydrogenated castor oil in a ratio of 30:0 has improved the reaction efficiency, shortening the reaction time by half, to only 1-2 hours instead of 3-5 hours if used alone.

The microemulsion obtained by the procedure of the present invention has a pH of 7-7.4. With this pH, the micelles are stable since the linkage between andrographolide and the carrier material is kept in dispersion in this neutral environment, while the microemulsion system has pH<7 then this linkage weakens resulting in degradation of the nano andrographolides in the digestive tract.

The mixture is homogenized by injection through a 30 Mpa (300 bar) high-pressure homogenizer. The homogenization of the suspension is to reduce the size of particles in the dispersed phase and evenly distribute them in the continuous phase to limit phase separation under the effect of gravity, to ensure uniformity and stability of the solution, and to increase product life.

(vi) Step 6: filtering the product by injection through a nanofilter system before filling and packing to remove excess impurities and ensure solution uniformity and stability.

The nanofilter system is a system specifically designed by the inventors to ensure the homogeneity of the finished product, remove impurities, and increase product quality. The filter system comprises a 100 nm pore size filter layer, a 60 Mpa (600 bar) high-pressure pump system to push the compounds through the filter layer, and a delivery body system. Particles and impurities larger than 100 nm will be captured on the filter membrane, the product obtained according to the invention is a homogeneous product.

The carrier system obtained by the process of the present invention has a pH of 7-7.5. With this pH, the micelles are stable since the bond between andrographolide and the carrier material is kept in dispersion in this neutral environment, while the nano carrier system has pH <7, then this bond weakens resulting in degradation of the nano andrographolide particles in the digestive tract.

The andrographolide carrier system obtained by the process of the present invention with HLB (hydrophilic lipophilic balance of 0-40) of 13-18 is a hydrophilic carrier system. The carrier system comprises non-aggregated hydrophilic micelles containing andrographolide, with a particle size less than 100 nm, so it may easily permeate across cell membrane to take effect and increase the solubility of andrographolide in water, thereby enhancing the bioavailability thereof.

The carrier system obtained by the process of the present invention allows the delivery of the active agents and controlled-release of andrographolide when administered orally, adhesion to the mucosa, and targeted release upon application.

In addition, the carrier system of this invention can be applied to many other active agents other than andrographolide, which allows to deliver active agents and targeted- and controlled-release similar small molecules.

EXAMPLES

Example: Production of 630 g of Andrographolide Carrier System

A dispersed phase was prepared by dissolving 80 g of andrographolide in 100 g of ethanol with a KIA—Germany C-MAG HS 4/7/10 magnetic hotplate stirrer at 400 rpm in combination with heating to 50° C. for 6 hours, to obtain 180 g of the dispersed phase.

A carrier comprising 120 g PEG was prepared by mixing in Labtech LWB-106D thermostatic bath, 1200 W, at 60° C. for 15 minutes.

120 g of the carrier was added to 180 g of the dispersed phase, this carrier-dispersed phase mixture continued to be heated to 50° C. and stirred at 600 rpm for 40 minutes using the KIA—Germany C-MAG HS 4/7/10 magnetic hotplate stirrer.

Bonds were formed to attach mucoadhesion enhancers onto the surface structure of the encapsulating layer by adding 10 g poly (acrylic acid) to the mixture, with stirring at 400 rpm for 30 minutes. At the end of this stage, 310 g was obtained.

Then the mixture was brought to room temperature, slowly added 5 g hydroxypropyl methylcellulose (HPMC), while stirring vigorously until homogeneous.

Heating continued until the temperature reached 50° C., 430 g of a mixture of Polysorbate 80 and PEG-40 hydrogenated castor oil (in a mass ratio of (25-35):(65-75)) was added to the carrier-dispersed phase mixture obtained above (in a mass ratio of 40:60) (because vacuum evaporation removed the ethanol solvent, the weight of the mixture excluding ethanol was 215 g), with further stirring at 500 rpm under vacuum, wherein the reaction temperature was kept at 50° C. for 1 hour.

The suspension mixture was homogenized by injection through a 30 Mpa high-pressure homogenizer with a maximum homogenization pressure of 30 MPa.

Filtration was performed through a nanofilter system to obtain about 630 g of andrographolide carrier system (excluding the amount removed and lost during the performance, the total loss of about 2%). The andrographolide carrier system obtained from this example was a stable, homogeneous mixture that ensured a particle size <100 nm.

By UV-vis spectroscopies, the inventors found that the peak positions of the andrographolide ingredient and the andrographolide carrier system were completely matching. This showed that the carrier system obtained by the process of the present invention still retained andrographolide structure and activity during nanoization. UV-vis spectrocopies were used to quantify the andrographolide content in the carrier system: The results showed that the concentration of andrographolide in the andrographolide carrier system was about 8-12%.

Figure 2:
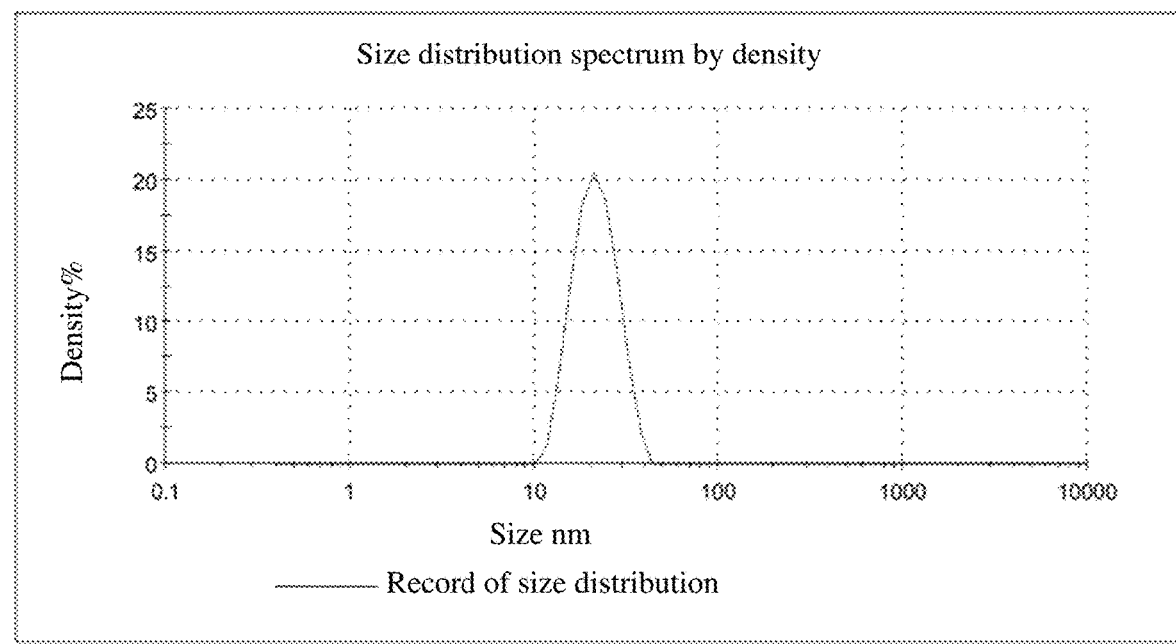
FIG. 2 shows a SEM spectrum of the size of andrographolide obtained by the process for producing of an andrographolide carrier system of the present invention.

Size measurement of nano andrographolides was conducted by scanning electron microscope TEM (transmission electron microscopy, abbreviated: TEM) as shown in FIG. 2, showing that the particle size was about 12-70 nm, which accounted for 100% of the solution.

Size measurement by DLS: Particles suspended in a liquid continuously undergo random motion, and the size of the particles directly affects their speed. Small particles move faster than larger ones. In DLS, light passes through a specimen, and scattered light is detected and recorded at a certain angle.

Zeta potential or dynamic potential: the potential between the dispersed phase and the dispersion medium.

| Size (nm, according to TEM) | Size (nm, according to DLS) | Zeta potential (mV) | Stability (month(s)) | Water solubility |
|---|---|---|---|---|
| 12-70 | 12-70 | −40 | >12 | Good water solubility, after dissolution in water, the system stabilized >30 days |

The above results showed that the andrographolide carrier system of the present invention comprised micelles smaller than 100 nm and had high stability (>12 months) and good water solubility, and, after dissolution in water, the system stabilized >30 days.

FIG. 1 is a picture comparing the water-dispersability between known 99% andrographolide and the nano andrographolide obtained by the process of the present invention, in which bottle A showed the known 99% andrographolide dispersed in water, and bottle B showed the nano andrographolide obtained by the process of the present invention. FIG. 1 shows that the known 99% andrographolide was insoluble in water, where particles were suspended in water, and the solution was slurry, deposited at the bottom of the bottle (BA) (A mói chính xác) over time; nano andrographolide obtained by the process of the present invention was completely dispersed in water, forming a transparent and homogeneous solution (AB).(B mói chính xác)

FIG. 2 shows the SEM spectrum of the size of nano andrographolide obtained by the process of the present invention. It was found that the average particle size was about 25.03 nm with a diameter of 24.06 and a density of 100%.

The following table shows the measurements:

|  |  | Diameter (nm) | Density % | Width (nm) |
|---|---|---|---|---|
| Average particle size (d · nm): 24.06 | Spectral Peak 1 | 25.03 | 100.0 | 5.785 |
| Pdl: 0.118 | Spectral Peak 2 | 0.00 | 0.00 | 0.00 |
| Shielding capacity: 0.940 | Spectral Peak 3 | 0.00 | 0.00 | 0.00 |
| Rating result: good | | | | |

Advantageous Effects of Invention

The process for producing an andrographolide carrier system of the present invention has succeeded in producing a carrier system with uniform andrographolide micelles smaller than 100 nm, with good solubility in water while retaining andrographolide structure and activity during nanoization, improving the limitations of andrographolide.

The agents used in process for producing the nano andrographolide carrier system, which are dispersed well in water, are highly safe and non-toxic, and have fewer side effects, so the nandrographolide carrier system obtained by the process of the present invention is highly safe when used.

The carrier system obtained by the process of the present invention allows to deliver active agents and controlled-release andrographolide when administered, especially orally, increase mucoadhesion ability, release with target, and increase absorbability of the active agents.

In addition, the carrier system obtained by the process of the present invention can be applied to many active agents other than andrographolide to deliver active agents and targeted- and controlled-release similar small molecules.

The process of the present invention is simple, easy to perform, and suitable for current practice.

We claim:

1. A method for producing an andrographolide carrier system for pharmaceutical composition, oral administration and other means, that allows for drug delivery of targeted- and controlled-release of andrographolide molecules, comprising:
  (i) preparing a dispersed phase by dissolving andrographolide in ethanol in solvent in a mass ratio of andrographolide to ethanol of 6-10:8-12 by a stirrer at 300-500 rpm while heating to 40-60 degrees Celsius for 4-8 hours;
  (ii) preparing an inner encapsulating carrier layer to protect active ingredient by heating liquid PEG (polyethylene glycol) to 60-80 degrees Celsius, with constant stirring for 15-30 minutes;
  (iii) forming a protective encapsulating layer of the active agent by adding the inner encapsulating carrier layer to the dispersed phase, with further heating of the carrier-dispersed phase mixture to 40-60 degrees Celsius while stirring at 400-800 rpm for 30-60 minutes;
  (iv) forming bonds to attach mucoadhesion enhancers onto the surface structure of the protective encapsulating layer by adding poly(acrylic acid) to the mixture in a mass ratio of 1-20:85-95, stirring at 400-800 rpm for 30-60 minutes to attach the poly (acrylic acid) onto the surface of the protective encapsulating layer, and then bringing the mixture to room temperature, slowly adding hydroxypropyl methylcellulose to the mixture in a mass ratio of 1-10:85-95, thereby increasing the expansion coefficient, adhesion force, and improving the release of adhesive poly(acrylic acid), and stirring vigorously the mixture until homogeneous;
  (v) heating the mixture until the temperature reaches 50 degrees Celsius, adding Polysorbate 80 and PEG-40 hydrogenated castor oil in a mass ratio of 25-35:65-75, to the carrier-dispersed phase mixture obtained in step (iv) in a mass ratio of 40:60, with further stirring at 500-700 rpm under vacuum, wherein the reaction temperature is kept at 50-80 degrees Celsius for 1-2 hours, controlling the quality of the resulting product by water dissolution and transparency measurement, and then continue heating and measuring transparency every 30 minutes until transparency is observed to quench the reaction, then homogenizing the mixture by injection through a 30Mpa (300 bar) high pressure homogenizer;
  (vi) filtering the product by injection through a nanofilter system before filling and packing, controlling quality of the resulting product by water dissolution and transparency measurement.

* * * * *